United States Patent
Goyal et al.

(10) Patent No.: US 10,343,148 B2
(45) Date of Patent: Jul. 9, 2019

(54) MIXED METAL OXIDE CATALYSTS AND METHODS FOR OLEFIN PRODUCTION IN AN OXIDATIVE DEHYDROGENATION REACTION PROCESS

(71) Applicant: Southern Research Institute, Birmingham, AL (US)

(72) Inventors: Amit Goyal, Durham, NC (US); Jadid Samad, Durham, NC (US)

(73) Assignee: SOUTHERN RESEARCH INSTITUTE, Birmingham, AL (US)

( * ) Notice: Subject to any disclaimer, the term of this patent is extended or adjusted under 35 U.S.C. 154(b) by 0 days.

(21) Appl. No.: 15/366,279

(22) Filed: Dec. 1, 2016

(65) Prior Publication Data

US 2018/0154341 A1    Jun. 7, 2018

(51) Int. Cl.

| | |
|---|---|
| *B01J 21/08* | (2006.01) |
| *B01J 23/26* | (2006.01) |
| *B01J 23/00* | (2006.01) |
| *B01J 23/745* | (2006.01) |
| *B01J 23/755* | (2006.01) |

(Continued)

(52) U.S. Cl.
CPC ............... *B01J 23/866* (2013.01); *C07C 5/48* (2013.01); *C07C 2521/06* (2013.01); *C07C 2523/745* (2013.01); *C07C 2523/755* (2013.01); *C07C 2523/86* (2013.01); *Y02P 20/52* (2015.11)

(58) Field of Classification Search
CPC . B01J 21/066; B01J 21/08; B01J 23/26; B01J 23/40; B01J 23/6522; B01J 23/745; B01J 23/755; B01J 23/862; B01J 23/866; B01J 23/8906; B01J 23/892; B01J 2219/00002; B01J 2231/70; B01J 2231/76; C07C 5/48; C07C 2521/06; C07C 2521/08; C07C 2523/86; C07C 2523/26; C07C 2523/40; C07C 2523/652; C07C 2523/745; C07C 2523/755
USPC .................................................. 502/313–316
See application file for complete search history.

(56) References Cited

U.S. PATENT DOCUMENTS 3,356,750 A * 12/1967 Bojanowski .......... C07C 17/357
                                                                570/153
3,424,808 A    1/1969 Brewer et al.
(Continued)

FOREIGN PATENT DOCUMENTS

WO    WO-2011/119203 A1    9/2011

OTHER PUBLICATIONS

Ansari, M.B., et al., "Carbon dioxide utilization as a soft oxidant and promoter in catalysis." Energy & Environmental Science, vol. 5(11): 9419-9437 (2012).

(Continued)

*Primary Examiner* — Patricia L. Hailey
(74) *Attorney, Agent, or Firm* — Ballard Spahr LLP (57) ABSTRACT

A catalyst structure includes a plurality of metal oxides formed on a support, where the support includes zirconia and/or silica. The metal oxides include at least three metals selected from the group consisting of chromium, iron, nickel, and a platinum group metal. The catalyst structure can be used in an oxidative dehydrogenation (ODH) reaction process for converting an alkane to an olefin. In some embodiments, carbon dioxide utilized in the ODH reaction process is obtained from a flue gas derived from a fossil fuel burning power plant.

22 Claims, 3 Drawing Sheets

(51) Int. Cl.
    *B01J 23/86*     (2006.01)
    *C07C 5/48*      (2006.01)

(56) References Cited

U.S. PATENT DOCUMENTS

| | | | | |
|---|---|---|---|---|
| 3,502,739 | A * | 3/1970 | Begley | C07C 5/3335 585/621 |
| 3,840,471 | A * | 10/1974 | Acres | B01D 53/9413 502/177 |
| 4,029,738 | A | 6/1977 | Courty et al. | |
| 4,134,860 | A * | 1/1979 | Hindin | B01J 37/0215 502/327 |
| 4,162,234 | A | 7/1979 | Grasselli et al. | |
| 4,278,566 | A * | 7/1981 | Hensley, Jr. | B01J 23/8878 208/145 |
| 6,777,371 | B2 * | 8/2004 | Liu | B01J 23/76 502/104 |
| 2003/0165424 | A1 | 9/2003 | Ramani et al. | |
| 2003/0208095 | A1 * | 11/2003 | Budin | B01J 23/52 585/658 |
| 2005/0124841 | A1 * | 6/2005 | Rapier | C07C 5/48 585/658 |

OTHER PUBLICATIONS

Deng, S., et al., "Activity and characterization of modified Cr 2 O 3/ZrO 2 nano-composite catalysts for oxidative dehydrogenation of ethane to ethylene with CO 2," Journal of Molecular Catalysis A: Chemical, vol. 268(1): 169-175 (2007).

Deng, S., et al., Oxidative dehydrogenation of ethane to ethylene with CO2 over Fe—Cr/ZrO2 catalysts. Industrial & Engineering Chemistry Research, 48(16), 7561-7566 (2009).

Dury, et al.,"The active role of CO2 at low temperature inoxidation processes:the case of the oxidative dehydro genation of propane on NiMoO4 catalysts," Applied Catalysis A: General, vol. 242(1): 187-203 (Mar. 2003).

Ewbank, J.L., et al.,"Effect of metal-support interactions in Ni/Al 2 O 3 catalysts with low metal loading for methane dry reforming," Applied Catalysis A: Genera, vol. 494: 57-67 (2015).

Gallon, K; "Ethane Prices Fell after a 4-Week Rally_ Impact on MLPs," Market Realist; http://marketrealist.com/2016/05/ethane-prices-fell-4-week-rally-impact-mlps/, (May 9, 2016).

Johnson, Creative Destruction, Chemistry & Industry, Issue 1, (Jan. 13, 2014), https://www.soci.org/chemistry-and-industry/cni-data/2014/1/creative-destruction, pp. 1-3.

Kawi, S., and T.J. Jennings, "CO2 as an Oxidant for High-Temperature Reactions." Frontiers in Energy Research: Carbon Capture, Storage, and Utilization, vol. 3, Article 13: 1-17 (2015).

Maffia et al., Techno-Economic Analysis of Oxidative Dehydrogenation Options, Spring Science and Business Media, (2016). Topics in Catalysis: 1-7.

Mukherjee et al., Co2 as a Soft Oxidant for Oxidative Dehydrogenation Reaction: An Eco Benign Process for Industry, Journal of CO2 Utilization, vol. 16, (Dec. 2013), pp. 301-312.

Nieto et al., Promoted NiO Catalysts for the Oxidative Dehydrogenation of Ethane, topics in Catalysis, 57 (2014), pp. 1248-1255.

Ren et al., Olefins from conventional and heavy feedstocks: Energy use in steam cracking and alternative processes, Energy, vol. 31, Issue 4, (Mar. 2006), https://doi.org/10.1016/j.energy.2005.04.001, pp. 425-451.

Seddon et al., C2: Ethylene Price History and Trends, Duncan Seddon & Associates Pty. Ltd. (Sep. 2012), http://www.duncanseddon.com/ethylene-price-history-and-trends/, p. 1.

Shimekit et al., Natural Gas Purification Technologies—Major Advances for CO2 Separation and Future Directions, INTECH Open Access Publisher, Chapter from the book Advances in Natural Gas Technology, pp. 235-270 (2012).

Wang et al., Oxidative Dehydrogenation of Ethane by Carbon Dioxide over Sulfate-Modified Cr2O3/SiO2 Catalysts, Department of Surface Chemistry, National Institute of Materials and Chemical Research, Japan, Catalysis Letters 63 (1999), pp. 59-64.

Wang et al., Dehydrogenation of Ethane with Carbon dioxide over Supported Chromium Oxide Catalysts, Applied Catalysis A: General, vol. 196, Issue 1, (Mar. 27, 2000), pp. 1-8.

Qiao et al., Oxidative Dehydrogenation of Ethane to Ethylene over Ni—Nb—M—O Catalysts: Effect of Promoter Metal and CO2-Admixture on the Performance, Catalysis Today, vol. 264, (Apr. 15, 2016), pp. 114-151.

Anonymous, U.S. Energy Information Administration (EIA), Frequently Asked Questions, How much carbon dioxide is produced per kilowatthour when generating electricity with fossil fuels?, Last updated (Mar. 21, 2017), https://www.eia.gov/tools/faqs/faq.php?id=74&t=11, pp. 1-2.

Anonymous, US Ethane and Ethylene Exports & Markets Report, Petrochemical Update, (Nov. 30, 2015), pp. 1-6.

Anonymous, Expansion Brings Jobs and Air Quality Fears, Will Pennsylvania See the Same with a Beaver County Plant, Shale Gas Fuels Gulf's Chemical Industry, The Alleghany Front, (Oct. 18, 2013), http://archive.alleghanyfront.org/story/shale-gas-fuels-gulfs-chemical-industry.html, pp. 1-10.

Anonymous, US and China Driving Global Ethylene Capacity to Record 208 Million Tons per Year by 2017, says GlobalData, http://energy.globaldata.com/media-center/press-releases/oil-and-gas/us-and-china-driving-global-ethylene-capacity-to-record-208-million-tons-per-year-by-2017-says-globaldata, (Dec. 10, 2014), pp. 1-2.

Anonymous, Ethylene, Chemical Economics Handbook (CEH), IHS Markit, (May 2017), https://www.ihs.com/products/ethylene-chemical-economics-handbook.html, pp. 1-5.

Anonymous, Petrochemicals Market Analysis By Product (Ethylene, Propylene, Butadiene, Benzene, Xylene, Toluene, Vinyls, Styrene, Methanol) By Region (North America, Europe, China, Middle East, Africa, Latin America) And Segment Forecasts, 2014-2025, (Oct. 2016), http://www.grandviewresearch.com/industry-analysis/petrochemical-market, pp. 1-110.

Anonymous, Petrochemical Outlook, Challenges and Opportunities, Prepared for: EU-OPEC Energy Dialogue, (Dec. 2014), https://ec.europa.eu/energy/sites/ener/files/documents/OPEC%20presentation.pdf, pp. 1-39.

Anonymous, Month Energy Review, U.S. Energy Information Administration, DOE/EIA-0035(Aug. 2016), (Aug. 26, 2016), www.eia.gov/mer, pp. 1-239.

Dietrich, US Front-Month Spot Ethylene Prices Up On Tightness, ICIS News, https://www.icis.com/resources/news/2016/03/08/9977169/us-front-month-spot-ethylene-prices-up-on-tightness/, (Mar. 8, 2016), p. 1.

International Search Report and Written Opinion dated Feb. 9, 2018 by the International Searching Authority for Patent Application No. PCT/US2017/063675, which was filed on Nov. 29, 2017 (Inventor—Goyal et al.; Applicant—Southern Research Institute; (8 pages).

* cited by examiner

FIG. 3

MIXED METAL OXIDE CATALYSTS AND METHODS FOR OLEFIN PRODUCTION IN AN OXIDATIVE DEHYDROGENATION REACTION PROCESS

FIELD OF THE INVENTION

The present invention relates to catalysts that are useful for an olefin production process. The present invention further relates to a process for forming alkenes or olefins such as ethylene utilizing a source of carbon dioxide, e.g., from a flue gas derived from a fossil fuel burning power plant and lower alkanes such as ethane from a source, e.g. ethane derived from natural gas.

BACKGROUND

Ethylene, due to its wide range usage in the manufacture of a number of different types of products (e.g., plastics, polymer, fibers, packaging materials, etc.), is the most commercially produced organic chemical in the world with a present global capacity of 334 billion pounds and the expectation to rise between 400 and 450 billion pounds within the next number of years. Other olefins, such as propylene and its derivatives, are also in increasing demand.

Historically, alkenes or olefins such as ethylene have been produced from petroleum feedstock through naphtha cracking. However, the naphtha cracking process requires a significant amount of energy and capital cost to yield the desired olefins. Due to the increased availability of natural gas (and thus ethane) in the United States, ethane has been increasingly used as feedstock for ethylene production. Conventional steam cracking plants accept ethane or naphtha as feed which are preheated and mixed with steam at very high temperatures (e.g., about 750-900° C.) in tubular reactors. Thus they are converted to low relative molecular mass alkenes. With ethane as feedstock in steam cracking, the following reaction takes place on ethane:

$C_2H_6 = C_2H_4 + H_2$ (Main reaction) $\Delta H° = 137$ kJ/mol $C_2H_6 + H_2 = 2CH_4$ (Side reaction)

Also, the products from steam cracking plants require complex separation trains to separate and recover methane, $H_2$, propane, propylene, butane, butylene and steam. Therefore, steam cracking (both ethane and naphtha) is a very energy intensive process. Specific energy consumption (SEC) from steam cracking process is 17-21 GJ/ton ethylene. Approximately 70% of the production costs in typical ethane- or naphtha-based plants is contributed by the energy cost. Due to large scale of production world-wide, energy consumption for ethylene alone accounts for about 1% of the world's annual energy consumption. Moreover, steam cracking process currently accounts for approximately 180-200 million tons of $CO_2$ emission world-wide (1.0-1.2 lb $CO_2$/lb ethylene). Due to such large magnitude of production of ethylene, any reduction on the energy requirement will be highly impactful.

Accordingly, it would be desirable to provide a production process for ethylene (or other olefins) that utilizes ethane and is further more energy efficient in relation to conventional olefin production processes.

SUMMARY OF THE INVENTION

In example embodiments, a catalyst structure comprises a plurality of metal oxides formed on a support, where the support comprises zirconia and/or silica. The metal oxides comprise at least three metals selected from the group consisting of chromium, iron, nickel, and a platinum group metal.

In other example embodiments, the catalyst structure can be provided within an oxidative dehydrogenation (ODH) reactor for converting an alkane to an olefin (e.g., converting ethane to ethylene).

In further example embodiments, a method of converting an alkane to an olefin via oxidative dehydrogenation (ODH) reactions comprises providing $CO_2$ and an alkane within one or more input gas streams to an ODH reactor that includes the catalyst structure, producing an olefin in the ODH reactor, and providing an output stream from the ODH reactor that comprises the olefin.

In some example embodiments, the carbon dioxide, which is used as a reactant in the ODH reaction process, can be obtained from a flue gas derived from a fossil fuel burning power plant.

The above and still further features and advantages of embodiments of the present invention will become apparent upon consideration of the following detailed description thereof, particularly when taken in conjunction with the accompanying drawings wherein like reference numerals in the various figures are utilized to designate like components.

BRIEF DESCRIPTION OF THE DRAWINGS

Like reference numerals have been used to identify like elements throughout this disclosure.

DETAILED DESCRIPTION

In accordance with the present invention, olefins (e.g., ethylene, propylene, butylene, etc.) are produced via an oxidative dehydrogenation (ODH) reaction process in which carbon dioxide is used as a "soft oxidant" along with one or more metal oxide catalysts that optimize the conversion of an alkane to an olefin. As described herein, the metal oxide catalysts comprise four or more metal oxides. In particular, metal oxide catalysts can include metal oxides comprising three or more selected from the group consisting of chromium, iron, nickel, and a platinum group metal (e.g., platinum, palladium, ruthenium and/or rhodium), where the three or more metal oxides are supported on a substrate comprising zirconia, silica or a combination of silica and zirconia.

The ODH reaction is more thermodynamically favorable for producing olefins from alkanes in relation to the conventional energy intensive techniques of steam cracking. An oxidant is generally required for the ODH reaction to proceed, producing the olefin with water and abstracted hydrogen ($H_2$) from the alkane of interest. The oxidizing ability for carbon gasification is on the following order (with $O_2$ having the greatest oxidizing ability): $O_2 > H_2O > CO_2 > H_2$. While the use of oxygen as the oxidant can effectively reduce the reaction temperature and inhibit coking, it can also result in low selectivity of the olefin species of interest due to production of $CO_x$ species and the need to remove excess heat. Carbon dioxide has been found to be more useful as a "soft" oxidant (softer than $O_2$) for the ODH process that prevents deep oxidation while being a suitable medium for the endothermic dehydrogenation reaction. The following ODH reactions take place for producing ethylene from a hydrocarbon feed including ethane. However, as previously noted, the ODH process utilizing catalysts as described herein can also be used for producing other olefins from alkanes (e.g., propylenes and butylenes such as butadiene).

Overall reaction:

$$C_2H_6 + CO_2 \rightarrow C_2H_4 + CO + H_2O \quad \Delta H° = 134 \text{ kJ/mol} \qquad (1)$$

The overall reaction can proceed in the following two steps:

$$C_2H_6 \rightarrow C_2H_4 + H_2 \quad \Delta H° = 137 \text{ kJ/mol} \qquad (2)$$

$$CO_2 + H_2 \rightarrow CO + H_2O \qquad (3)$$

The following two reactions are undesired side reactions:

$$C_2H_6 + H_2 \rightarrow 2CH_4 \qquad (4)$$

$$C_2H_6 + 2CO_2 \rightarrow 4CO + 3H_2 \quad \Delta H° = 431 \text{ kJ/mol} \qquad (5)$$

In presence of oxygen the ODH reaction becomes fully exothermic. Hence, the reaction could proceed at lower temperatures using $O_2$:

$$C_2H_6 + 0.5 O_2 \rightarrow C_2H_4 + H_2O \quad \Delta H° = -105 \text{ kJ/mol} \qquad (6)$$

However, since $O_2$ is a strong oxidant, its use in the ODH process can result in complete oxidation, thus promoting $CO_2$ formation and reducing selectivity to ethylene. Furthermore, certain sources of $CO_2$ such as flue gas comprise of low amount of $O_2$ which can be partially utilized to heat the feed streams (combustion) and residual $O_2$ can be used to promote ODH reaction.

It has been found that the best methods for forming ethylene (or another olefin) via an ODH process is using carbon dioxide as a "soft" oxidant or, alternatively, a combination or mixed oxidant feed of $CO_2/O_2$ at a ratio that maximizes ethylene yield and also reaction temperature.

The fixed costs, processing and operational costs for an ODH plant are much less in relation to conventional steam cracking plants that typically form olefins such as ethylene and propylene. For example, ODH plants and typically smaller in size (floor foot print) and require smaller and/or less equipment in relation to steam cracking plants and the cost of operation of the ODH plant is also smaller (less energy requirements). The ODH process further is more environmentally friendly in that it produces fewer greenhouse gas (GHG) emissions in relation to steam cracking processes.

However, while the ODH process has these advantages over the standard steam cracking process to form olefins, the ODH process has yet to gain large scale commercialization due to its lower olefin yield than standard steam cracking processes. For example, ODH processes that have been attempted to produce ethylene have only been able to achieve maximum ethylene yields of about 40% to 50% at high operating temperatures.

In accordance with the present invention, new metal oxide catalysts as described herein have been determined to be highly effective in the ODH reaction process to form olefins from alkanes, where the catalysts enhance the ODH reaction, increasing ethylene yields by as much as 60% or greater while operating at low to moderate temperatures that are at least about 200° C. less than the higher operating temperatures associated with known ODH reactions that convert alkanes to olefins.

A further advantage of the ODH reaction process is that carbon dioxide for use as the soft oxidant can be obtained from the flue gas resulting from the burning of a fossil fuel. In particular, the flue gas derived from a fossil fuel power station that burns coal, natural gas or petroleum to generate electricity can be used as a source of $CO_2$. In an example embodiment, the flue gas derived from a coal fired power plant can be used as the $CO_2$ source. The $CO_2$ that is generated from the coal or other fossil fuel burning processes and that is typically released as flue gas emissions can be instead used in the ODH reaction process (after optional removal of $SO_x$, $NO_x$, etc. from the flue gas), thus reducing the greenhouse gas (GHG) emissions from the fossil fuel burning process.

Figure 1:
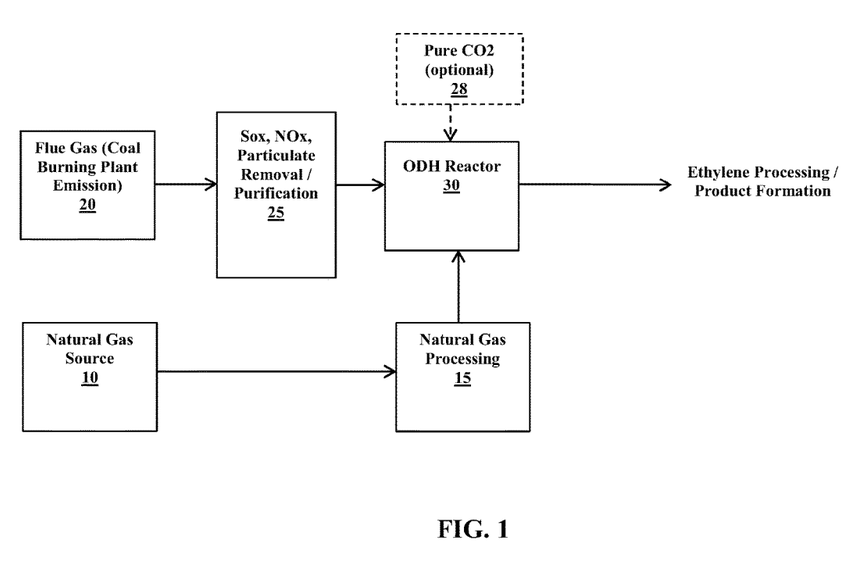
FIG. 1 is a schematic diagram showing a system for producing an olefin such as ethylene utilizing an oxidative dehydrogenation (ODH) reaction process in accordance with an example embodiment of the present invention.

An example embodiment of a system that facilitates production of ethylene via an ODH reaction (as represented by previously described Equations 1-3 and/or Equation 6) is depicted in the schematic diagram of FIG. 1. A natural gas source 10 provides the supply for the source of alkane, in particular ethane, as a reactant in the ODH reaction. Typical natural gas compositions include the following components at the following weight percentages:

TABLE 1

Typical Natural Gas Composition

| Component | Weight Percentage (%) |
|---|---|
| $CH_4$ | 87%-97% |
| $C_2H_6$ | 1.5%-7.0% |
| $C_3H_8$ | 0.1%-1.5% |

The natural gas can be processed at a station or plant 15 in any suitable manner to separate ethane (also propane) from other components in the natural gas stream so as to yield a gas stream that is, e.g., 90% by weight or greater ethane. For example, natural gas processing plant 15 can include one or more adsorption/absorption units to remove contaminants from the natural gas, one or more fractionating columns (e.g., to separate ethane from propane and higher molecular weight hydrocarbons), any selected number or types of filtration units, etc. to effectively separate ethane from other components within the natural gas stream.

The carbon dioxide source for the ODH process can be provided from a flue gas, e.g., from a coal fired power plant 20. Certain components (e.g., $SO_x$, $NO_x$ and particulate matter) can be removed at a purification station or plant 25 prior to delivery to the ODH reactor 30. The purification plant 25 can include any suitable equipment (e.g., adsorption units, filters, molecular sieves, etc.) to effectively remove components such as $SO_x$, $NO_x$, etc. from the flue gas. The purification plant 25 can provide a purified gas that includes components in the following typical representative ranges:

TABLE 2

Purified Flue Gas

| Component | Weight Percentage (%)/parts per million (ppm) |
|---|---|
| $CO_2$ | 12.5%-12.8% |
| $H_2O$ | ≤6.2% |
| $O_2$ | ≤4.4% |

TABLE 2-continued

Purified Flue Gas

| Component | Weight Percentage (%)/parts per million (ppm) |
|---|---|
| CO | ≤50 ppm |
| $NO_x$ | 420 ppm |
| $SO_2$ | 420 ppm |
| $N_2$ | 76%-77% |

A further source of $CO_2$ can optionally be provided, e.g., from a pure $CO_2$ supply source 28. However, it is desirable to utilize $CO_2$ that is already available from the flue gas of a fossil fuel power station that burns a fossil fuel (e.g., a coal fired power plant), since this minimizes the environmental impact of GHG emissions that such hydrocarbon burning systems generate as a by-product.

The source of ethane from the natural gas processing plant 15 and the $CO_2$ (and/or $O_2$) source from the flue gas purification plant 25 (and/or optionally from another $CO_2$ source 28) is provided to the ODH reactor 30. The ODH reactor includes a catalyst bed including one or more catalysts as described herein that facilitate reactions as set forth in Equations 1-3 ($CO_2$ as oxidant) and/or Equation 6 ($O_2$ as oxidant) so as to produce ethylene. The ODH reactor 30 operates at a moderate temperature range from about 450° C. to about 650° C. and at about standard pressure (about 1 atm).

The ODH reactor 30 can comprise a fixed bed reactor that includes a feed section for receiving as input the ethane gas stream (from the natural gas processing plant 15) and the $CO_2$ gas stream (from the purification plant 25), where the input gas streams can be controlled independently via mass flow controllers. The input gas streams can be mixed together (e.g., via a static gas mixer) and heated in a preheating section prior to being delivered for contact with a catalyst bed within a reaction section of the ODH reactor 30. A by-pass line can also be provided within the gas feed line (e.g., downstream from the static mixer) to direct a sample portion of the mixed gaseous feed to an analyzer for analysis of the gas feed entering the reaction section.

The reaction section of the ODH reactor 30 includes a packed bed of particles comprising one or more of the catalyst structures as described herein. In particular, the reaction section further can include a reaction chamber that includes the packed bed of catalyst particles, a temperature controlled furnace (to maintain suitable temperature within the range of about 450° C. to about 650° C. within the reaction section), and a pressure regulator (to maintain standard pressure within the reaction section). The reaction chamber can comprise suitable dimensions based upon the size and scaling requirements for the ODH reactor 30 (e.g., based upon implementation of the ODH reactor with a particular coal fired power plant, flow rates and amounts of input gas streams, desired output flow rates and amounts of ethylene, etc.), where the catalyst can be crushed and sieved to form a suitable particle size for the packed bed. The catalyst particles can be mixed with an inert support (e.g., glass or SiC beads) to form the packed bed within the reaction section. Thermocouples and/or other suitable temperature measurement devices can be provided at any number of suitable locations within the packed bed in order to maintain a desired temperature within the reaction section of the ODH reactor 30.

The product stream emerging from the reaction section of the ODH reactor 30 can be passed through a condenser (for condensing water from the product stream). Optionally, a portion of the product stream can be analyzed (e.g., via gas chromatography) for component concentrations within the product stream.

The products within the product stream generated by the ODH reaction process are primarily ethylene, carbon monoxide and water. The output stream from the ODH reactor 30 can be further purified in any conventional or other suitable manner (e.g., using adsorption methods such as pressure or temperature swing adsorption, fractionation, membrane separation, etc.) to separate ethylene from other components (e.g., carbon monoxide, water, unreacted products such as ethane and carbon dioxide, etc.), where the ethylene can then be further processed at other suitable locations to form a variety of different plastic or polymer products for commercial and industrial use (e.g., plastic packaging materials and/or other products, polymers, synthetic fibers, etc.). Alternatively, ethane and ethylene can be maintained together and used as a feedstock for the formation of certain other products (e.g., ethylene epoxidation to form ethylene oxide, where the ethane is fed with ethylene in the feedstock to enhance heat dissipation during the exothermic reaction to form ethylene oxide). Ethylene and CO can also be used together in OXO and Carbonylation reactions to form other desired products (e.g., aldehydes, carboxylic acids, esters, ketones, etc.). Thus, the ethylene and CO products from the ODH reaction process are highly desirable platform compounds that serve as intermediate compounds for use in forming a wide range of chemical compounds for industrial and commercial purposes.

The system described in FIG. 1 can be partially integrated with a coal or other hydrocarbon burning plant. For example, the purification plant 25 and ODH reactor 30 can be integrated as downstream stations from the flue gas emission of a coal fired power plant 20. The ethane source obtained, e.g., from a natural gas supply, can be processed at plant 15 with the purified ethane source then being delivered (e.g., by transport vehicle) for input to the ODH reactor 30.

As previously noted, an ODH reaction process (with $CO_2$ and an alkane such as ethane as input feed streams) to produce ethylene (or other olefins) provides considerable start-up and operational cost reduction and a reduction in operational energy requirements (as well as environmental benefits by reducing GHG emissions) in relation to conventional steam cracking techniques. However, there has been a reluctance in switching from conventional practice to an ODH reaction process for producing ethylene from ethane due to the low ethylene yield (limit to about 50% at high temperatures) associated with the ODH process. The new catalyst structures described herein can improve ethylene yield from the ODH process, thus making it more economically feasible to utilize this process for ethylene (and other olefin) production.

Metal oxide catalysts useful for the ODH reaction process for forming an olefin such as ethylene include metal oxides comprising three or more metals selected from the group consisting of chromium, iron, nickel, and a platinum group metal such as platinum, palladium, ruthenium and/or rhodium, where the three or more metal oxides are supported on a substrate comprising zirconia, silica or a combination of silica and zirconia. The selection of specific metal oxides for combining to form catalysts useful for the ODH reaction are based upon the combination providing suitable functionalities, such as yielding a suitable selectivity, conversion and redox functionality in the ODH reactions, that result in an increased yield of ethylene at temperatures that are typical ODH reaction processes.

For example, certain metal oxide catalysts with redox properties such as molybdenum, chromium and vanadium-based oxides possess high catalytic activity for certain ODH reactions of hydrocarbons. In particular, chromium based catalysts exhibit excellent activity for the dehydrogenation of ethane and $CO_2$ and can promote such reactions leading to an increase in ethylene yield. The reaction paths occurring in the dehydrogenation of ethane by $CO_2$ utilizing chromium oxide as a catalyst can be as follows:

$$3C_2H_6 \rightarrow 3C_2H_4 + 3H_2 \quad (7)$$

$$3H_2 + 2CrO_3 \rightarrow 3H_2O + Cr_2O_3 \quad (8)$$

$$Cr_2O_3 + 3CO_2 \rightarrow 3CO + 2CrO_3 \quad (9)$$

In these reactions, $CO_2$ as oxidant enhances the regeneration of the reduced chromium sites (Equation 9) formed during the dehydrogenation of ethane and successive reduction with $H_2$, where $CrO_3$ represents the oxidized form and $Cr_2O_3$ represents the reduced form of the catalyst. The by-products of these reactions are CO and $H_2O$.

The use of another metal oxide catalyst, such as iron, cobalt, manganese, in combination with chromium oxide can improve the selectivity for ethylene, but the catalyst activity can also decline. For example, in presence of Fe—Cr, $Fe_3O_4$ can form during dehydrogenation of ethane which can promote a reverse water gas shift reaction.

Presence of a Group VIII metal e.g., Platinum, Nickel oxide have also been found to increase ethane conversion in the ODH reaction process. For example, in the presence of nickel oxide, ethane conversion increases to 90% or greater even at moderate temperatures of about 550° C. However, the selectivity for conversion to ethylene can be very low (<8%) with amounts of nickel oxide as low as 5%.

The support for a catalyst structure can also influence the selectivity of certain ODH reactions. For example, silica supported chromium oxide catalysts have been found to provide similar ethane conversion but higher selectivity to ethylene in relation to zirconium oxide supported chromium oxide catalysts, with the point of zero charge (PZC) being more acidic for the silica support (e.g., PZC is 1.0-2.0 for $Cr_2O_3/SiO_2$) in relation to the zirconium oxide support (e.g., PZC is 7.0 for $Cr_2O_3/ZrO_2$). However, the zirconium oxide support was found to have a higher turn-over number (TON) represented as activity per surface area in relation to the silica support for chromium oxide support structure.

In accordance with the present invention, it has been found that combining various metal oxides in suitable amounts on a zirconium oxide and/or silica support provides a synergistic effect in that it results in a much more effective catalyst structure that results in greater conversion and selectivity for ethylene at reduced temperatures of 450° C. to 650° C. In case of a mixed oxide support a composition range between 1% $ZrO_2$:90% $SiO_2$ to 90% $ZrO_2$:10% $SiO_2$ could be used to prepare the support.

Example catalyst structures formed in accordance with the present invention can include a combination of metal oxides comprising chromium, iron and nickel. In particular, the catalyst structures comprise a combination of NiO, $Fe_2O_3$ and $Cr_2O_3$ provided on a catalyst support comprising zirconia ($ZrO_2$) or a combination of silica and zirconia ($SiO_2/ZrO_2$), such that the catalyst structure comprises a combination of NiO, $Fe_2O_3$, $Cr_2O_3$, $ZrO_2$ and/or $SiO_2$. In such embodiments, NiO is provided in an amount from about 0.01% to about 10% by weight of the catalyst structure, $Fe_2O_3$ is provided in an amount from about 0.01% to about 30% by weight of the catalyst structure, and $Cr_2O_3$ is provided in an amount from about 0.01% to about 30% by weight of the catalyst structure. In further example embodiments, NiO is provided in an amount of no greater than about 1% by weight of the catalyst structure, and each of $Fe_2O_3$ and $Cr_2O_3$ is provided in an amount of at least about 5% by weight of the catalyst structure.

A catalyst structure is formed in accordance with the present invention by wet impregnation of zirconia and/or silica particles that comprise the support with three or more metal oxides selected from the group consisting of nickel oxide, iron oxide, chromium oxide, and a platinum metal oxide. The metal oxides can be dissolved in aqueous solution, with the zirconia and/or silica support particles then being mixed into solution, followed by drying of the solution (by heating and/or calcination) to remove moisture such that the metal oxides are deposited on exposed surface areas of the support to form the catalyst support structures.

The combination of these metal oxides in the catalyst structure provides the redox functionalities of chromium oxide to enhance production of ethylene in the ODH reactions (e.g., promoting the reactions of Formulas 7-9), while nickel oxide promotes higher conversion of ethane and iron oxide promotes higher selectivity of ethylene. Further, providing a zirconia support or a combination of zirconia with silica further enhances ethane conversion and turn-over number (TON) or ethane converted per area of surface as well as ethylene selectivity and yield. The surface area of the catalyst structure defined by the zirconia and/or silica support can be in the range of about 20 m$^2$/g to about 1000 m$^2$/g. Such catalyst structures can increase the yield by 20% or more for conversion of an alkane (e.g., ethane) to an olefin (e.g., ethylene) using an ODH reaction process in comparison to other known ODH reaction techniques. In particular, the use of such catalyst structures can convert at least 60% of ethane to ethylene in an ODH reaction process (e.g., utilizing a system as depicted in FIG. 1).

Other metal oxides that can be provided as part of the catalyst structure as an alternative or as a supplement to nickel oxide include oxides of platinum group metals such as platinum (e.g., $PtO_2$), palladium (e.g., PdO) and ruthenium (e.g., $RuO_2$). Any one or more of such platinum metal oxides can be combined in any manner with or without nickel oxide to enhance the functionalities of the catalyst structure so as to increase conversion of a particular alkane and selectivity and yield of a particular olefin for a particular series of ODH reactions.

Some examples are now described showing the formation of a specific catalyst structure of the present invention and its comparison in use with another known catalyst structure.

Example 1: Formation of 0.1 wt % NiO-5 wt % Fe2O3-10 wt % Cr2O3/ZrO2 Catalyst

Figure 2:
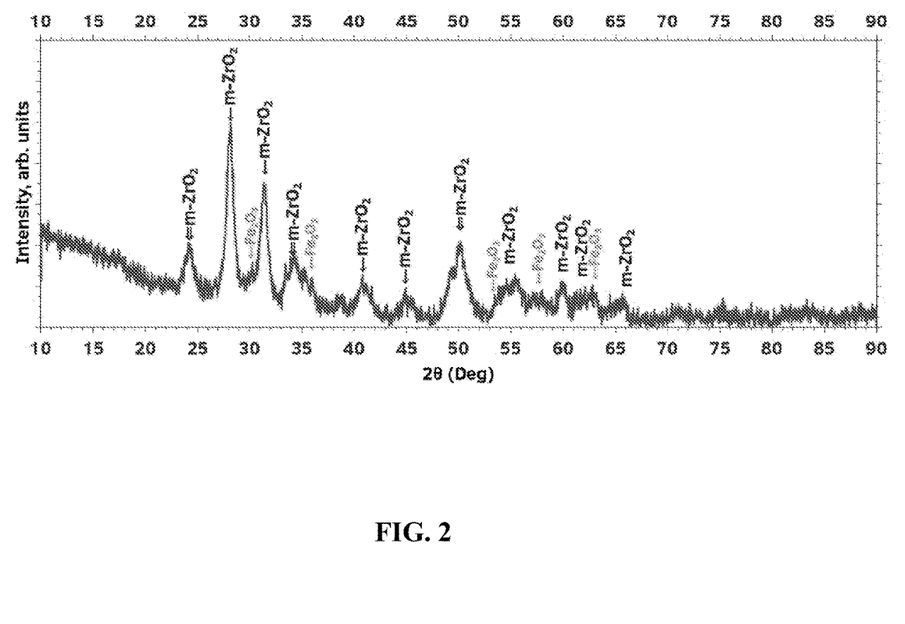
FIG. 2 is a plot of a wide angle X-ray diffraction (XRD) pattern of a metal oxide catalyst formed in accordance with an example embodiment of the present invention.

A 0.1 wt % NiO-5 wt % Fe2O3-10 wt % Cr2O3/ZrO2 catalyst was prepared via wet impregnation. First, 0.0195 g Ni(NO$_3$)$_2$.6H$_2$O, 1.76 g CrCl$_3$.6H$_2$O and 1.2727 g Fe(NO$_3$)$_3$.9H$_2$O were dissolved in 50 ml of deionized water. After proper mixing, powdered $ZrO_2$ was added to this solution and the resulting slurry was dried in a rotary evaporator at 60° C. The resulting sample was dried further in an oven at 100° C. and was subsequently calcined at 600° C. for 3 hours in static air. An x-ray diffraction (XRD) profile of the resulting sample is presented in FIG. 2. The XRD profile shows evidence of monoclinic zirconia and $Fe_2O_3$.

Figure 3:
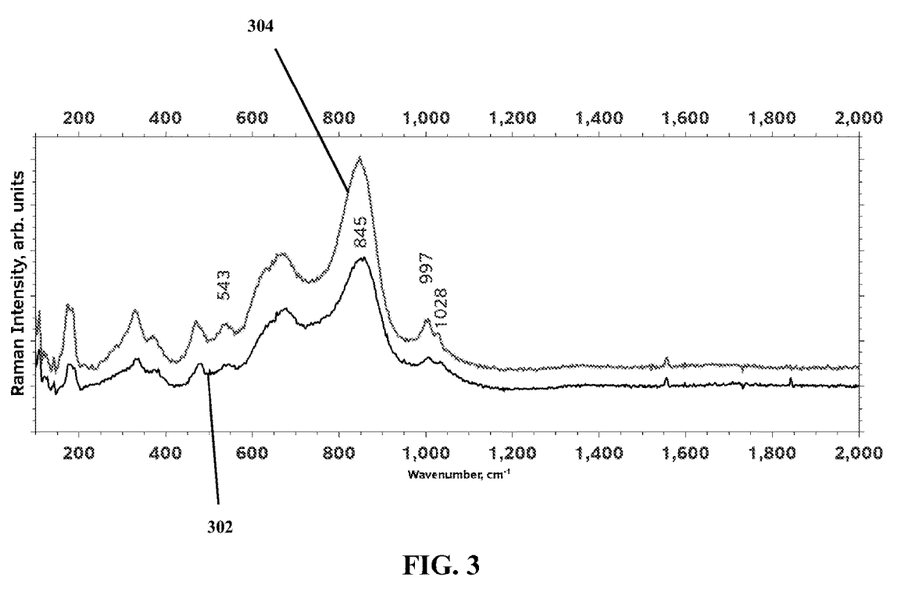
FIG. 3 is a plot of a Raman spectral pattern for the same catalyst of FIG. 2 both before and after use of the catalyst.

Presence of $Cr_2O_3$ was verified from the Raman spectra plot in FIG. 3 (where all of the labelled peaks in FIG. 3 can be attributed to chromium oxides). The low intensity Raman line marked at about 1550 cm-1 likely represents nickel oxide. Further, the two plots in the Raman spectra represent a fresh sample (plot 302) and a used sample (plot 304) (i.e., the sample has been used in the ODH reactor). Both plots are very similar, which demonstrates substantially no deactivation of the catalyst structure.

Example 2: Testing of Catalyst Structure of Invention

The catalyst structure from Example 1 was tested in a gas phase fixed bed reactor (e.g., an ODH reactor such as the type described in the embodiment of FIG. 1) operating at 550° C. and atmospheric pressure (about 1 atm). A gas feed total flow rate of 16 ml/min was used at a composition of 12.5% ethane, 37.5% $CO_2$ and remaining $N_2$. Two different values for gas hourly space velocity (GHSV) were used (4800 $h^{-1}$ and 3000 $h^{-1}$) by changing the flow rates. The experiments were conducted in a continuous reactor for a period of 6 to 8 hours. Effluent gases were analyzed using an online gas chromatograph equipped with a flame ionization detector (FID) and a thermal conductivity detector (TCD). Effluent gas samples were also collected using gas bags to conduct offline gas chromatography. Typical catalyst loading was 200 mg with SiC used as inert.

The results of the testing of the catalyst structure, including ethane conversion, ethylene selectivity and yield, and turn-over number (TON) (i.e., ethane converted per area of catalyst surface), are provided in Table 3 herein. For comparison purposes, two known catalyst structures are also listed in Table 3, where such catalyst structures are described by Deng et al., "*Activity and characterization of modified $Cr_2O_3/ZrO_2$ nano-composite catalysts for oxidative dehydrogenation of ethane to ethylene with $CO_2$.*" *Journal of Molecular Catalysis A: Chemical* 268.1 (2007): 169-175 (hereinafter referred to as "Deng").

TABLE 3

Comparison of Catalyst Structures

| Catalyst | $C_2H_6$ conversion (%) | $C_2H_4$ selectivity (%) | $C_2H_4$ yield (%) | TON (gm ethane converted/ $m^2 \cdot h$) × $10^3$ |
| --- | --- | --- | --- | --- |
| 10% $Cr_2O_3$-5 wt % $Fe_2O_3$/nano $ZrO_2$ [Deng] | 18.4 | 98.4 | 18.08 | 1.3 |
| 10% $Cr_2O_3$-5 wt % NiO/nanoZrO$_2$ [Deng] | 90.65 | 8.2 | 7.4 | 6.7 |
| 10% $Cr_2O_3$-5 wt % $Fe_2O_3$-0.1 wt % NiO/ZrO$_2$ Example 1 GHSV = 4800 $h^{-1}$ | 12.5 | 99 | 12.3 | 2.5 |
| 10% $Cr_2O_3$-5 wt % $Fe_2O_3$-0.1 wt % NiO/ZrO$_2$ Example 1 GHSV = 3000 $h^{-1}$ | 13.6 | 99 | 13.5 | 2.7 |

The $ZrO_2$ support used for the catalyst structure of Example 1 had a surface area of 40 $m^2/g$ after deposition, while the catalysts structures of Deng had a higher surface area (nano zirconia) of 171 $m^2/g$.

While the conversion of ethane for both the 10% $Cr_2O_3$-5 wt % NiO/nanoZrO$_2$ catalyst and the 10% $Cr_2O_3$-5% $Fe_2O_3$/nano $ZrO_2$ catalyst reported by Deng are greater than the conversion of ethane for the catalyst structure of Example 1 (10% $Cr_2O_3$-5 wt % $Fe_2O_3$-0.1 wt % NiO/ZrO$_2$), the actual rate presented as turn over number (activity per surface area) is, in fact, higher for the catalyst of Example 1. Further, the selectivity for ethylene for the catalyst structure of Example 1 is greater than either catalyst structure reported by Deng. In addition, the selectivity for ethylene remains high (99%) for the catalyst structure of Example 1 even at the higher flow rate (GHSV of 4800 $h^{-1}$).

This example demonstrates the enhanced effect of the catalyst structure due to the combination of chromium oxide with iron oxide and nickel oxide, with the amounts of each metal oxide being controlled to enhance the conversion, selectivity and yield for forming ethylene in the ODH reaction process.

Thus, the catalyst structures of the present invention enhance a process of forming an olefin such as ethylene from an alkane such as ethane utilizing $CO_2$ as a reactant, where the $CO_2$ can be obtained from the flue gas of a coal fired plant or from the effluent of any other hydrocarbon burning process. Upon removal of impurities such as $SO_x$ and $NO_x$ from the flue gas, the composition will comprise at least about 10% by weight $CO_2$ which can be fed as an oxidant reactant material to the ODH reactor. The flue gas will also contain $O_2$ (e.g., in amounts of as much as about 4%), which can also be used as an oxidant in the ODH reaction process (e.g., as described in relation to Equation 6) in combination with $CO_2$ to form olefins such as ethylene. Instead of trying to separate $O_2$ from $CO_2$ (which can be a difficult process) prior to input to the ODH reactor, the ODH reaction process can take advantage of the $O_2$ present in the input stream to obtain a desired $O_2:CO_2$ ratio (e.g., a $O_2:CO_2$ ratio of 1:10 to 1:1000) that increases catalyst activity and can further reduce reaction temperatures and/or increase alkane conversion, olefin selectivity and yield for a particular ODH reaction process.

In a similar manner, sulfur oxides (e.g., $SO_2$) can also have a positive effect in enhancing the ODH reaction process, such that in certain scenarios it may be desirable to maintain a desired amount of $SO_x$ within the processed flue gas for input to the ODH reactor. Thus, for certain ODH reactions, purification of the input $CO_2$ gas (e.g., flue gas effluent obtained from a coal fired plant) can be minimized since certain impurities may not impact or might even be beneficial for the ODH reaction process (depending upon the particular catalyst structure utilized and/or the type or types of olefins to be produced by the process).

Utilizing the catalyst structures of the invention in the ODH process results in a product stream from the ODH reactor that includes ethylene, CO and $H_2O$ as well as some portion of unreacted $CO_2$ and ethane. Any conventional and/or other suitable techniques (e.g., membrane separation, pressure and/or temperature swing adsorption) to separate CO and $CO_2$ from ethane and ethylene. Ethylene can further be separated from ethane using fractionation and/or any other suitable separation techniques. Alternatively, ethane and ethylene can be maintained together and used as a feedstock for the formation of certain other products (e.g., ethylene epoxidation to form ethylene oxide, where the ethane is fed with ethylene in the feedstock to enhance heat dissipation during the exothermic reaction to form ethylene oxide). Ethylene and CO can also be used together in OXO and Carbonylation reactions to form other desired products (e.g., aldehydes, carboxylic acids, esters, ketones, etc.).

Thus, the ethylene and CO products from the ODH reaction process are highly desirable platform compounds that serve as intermediate compounds for use in forming a wide range of chemical compounds for industrial and commercial purposes.

The ODH reaction process, which incorporates the use of catalyst structures in accordance with the present invention, can be easily integrated into a coal fired plant (as depicted, e.g., in the system of FIG. 1) with limited process equipment installation. This allows for the $CO_2$ (and $O_2$) containing flue gas to be used constructively in producing platform chemicals (e.g., ethylene and/or other olefins and CO) instead of releasing such flue gas components as GHG emissions to the environment. The use of the catalyst structures described herein in the ODH reaction process can result in a reduction in the operating temperature of at least 200° C. in relation to known ODH reaction processes for converting alkanes to olefins (where ODH reactor conditions, as described herein, can be in a moderate temperature range from about 450° C. to about 650° C.). Greenhouse gas emissions can be reduced by 35% or more when utilizing flue gas from coal fired plants as the $CO_2$ input feed source. The new catalyst structures described herein can further increase ethylene production yield to at least 60%, which is about 20% greater yield in relation to other known catalyst structures for ODH reactions that product ethylene (e.g., the catalyst structures described by Deng).

While flue gas streams are useful for the $CO_2$ input source for the ODH reactions described herein, the invention is not limited to using flue gas streams but instead can use $CO_2$ from any suitable supply source. For example, any $CO_2$ supply source that contains a suitable concentration of carbon dioxide (e.g., at least about 10% by weight of $CO_2$ in the gas stream) can be utilized as an input feed stream for the ODH reaction process described herein. Some non-limiting examples of other sources of $CO_2$ which can be utilized as feed streams to an ODH reaction process include any $CO_2$ waste stream from an industrial chemical producing plant, recycled $CO_2$ streams from oil recovery processes, etc.

While the invention has been described in detail and with reference to specific embodiments thereof, it will be apparent to one skilled in the art that various changes and modifications can be made therein without departing from the spirit and scope thereof.

Thus, it is intended that the present invention covers the modifications and variations of this invention provided they come within the scope of the appended claims and their equivalents.

What is claimed:

1. A catalyst structure comprising a plurality of metal oxides formed on a support comprising zirconia and/or silica, the metal oxides comprising at least three metals selected from the group consisting of chromium, iron, nickel, and a platinum group metal.

2. The catalyst structure of claim 1, wherein the platinum group metal is selected from the group consisting of platinum, palladium, ruthenium and rhodium.

3. The catalyst structure of claim 1, wherein the metal oxides comprise nickel oxide present in an amount from about 0.01% to about 10% by weight of the catalyst structure.

4. The catalyst structure of claim 3, wherein the nickel oxide is present in an amount of no greater than about 1% by weight of the catalyst structure.

5. The catalyst structure of claim 1, wherein the metal oxides comprise chromium oxide in an amount from about 0.01% to about 30% by weight of the catalyst structure.

6. The catalyst structure of claim 1, wherein the metal oxides comprise iron oxide in an amount from about 0.01% to about 30% by weight of the catalyst structure.

7. The catalyst structure of claim 1, wherein the metal oxides comprise chromium oxide in an amount of at least about 5% by weight of the catalyst structure, iron oxide in an amount of at least about 5% by weight of the catalyst structure, and nickel oxide in an amount of no greater than about 1% by weight of the catalyst structure.

8. The catalyst structure of claim 1, wherein the metal oxides comprise $Cr_2O_3$ in an amount of 10% by weight of the catalyst structure, $Fe_2O_3$ in an amount of 5% by weight of the catalyst structure, and NiO in an amount of 0.1% by weight of the catalyst structure.

9. The catalyst structure of claim 8, wherein the support comprises zirconia.

10. A system for conversion of an alkane to an olefin via an oxidative dehydrogenation (ODH) reaction process, the system comprising: an ODH reactor including the catalyst of claim 1; a first feed source comprising $CO_2$; and a second feed source comprising an alkane.

11. The system of claim 10, wherein the first feed source further comprises O.sub.2.

12. The system of claim 11, wherein the ratio of $O_2$ to $CO_2$ is between 1:10 to 1:1000.

13. The system of claim 10, wherein the first feed source comprises a flue gas emission from a fossil fuel power station that burns a fossil fuel to generate electricity.

14. The system of claim 13, wherein the second feed source comprises a natural gas feed that includes the alkane.

15. The system of claim 10, wherein the alkane comprises ethane, and the ODH reactor is configured to produce an output stream that comprises ethylene.

16. A method of converting an alkane to an olefin via oxidative dehydrogenation (ODH) reactions, the method comprising: providing $CO_2$ and an alkane within one or more input gas streams to an ODH reactor that includes the catalyst structure of claim 1; producing an olefin in the ODH reactor; and providing an output stream from the ODH reactor that comprises the olefin.

17. The method of claim 16, further comprising: producing CO within the ODH reactor; wherein the output stream further comprises CO.

18. The method of claim 16, wherein the $CO_2$ is provided in a gas stream that is derived from flue gas output from a fossil fuel power station.

19. The method of claim 18, wherein the alkane is obtained from a natural gas feed.

20. The method of claim 16, wherein the alkane comprises ethane, and the olefin comprises ethylene.

21. The method of claim 16, wherein the operating temperature of the ODH reactor is from about 450° C. to about 650° C.

22. The method of claim 16, further comprising: providing $O_2$ within the one or more input gas streams to the ODH reactor, wherein the ratio of $O_2$ to $CO_2$ within the one or more input gas streams is between 1:10 to 1:1000.

* * * * *